(12) United States Patent
Wintermark et al.

(10) Patent No.: US 7,580,737 B2
(45) Date of Patent: *Aug. 25, 2009

(54) METHOD AND APPARATUS FOR DETERMINING TREATMENT FOR STROKE

(75) Inventors: Max Wintermark, Lausanne (CH); Jean-Philippe Thiran, Lausanne (CH); Reto Antoine Meuli, Lausanne (CH)

(73) Assignee: Universite de Lausanne, Lausanne (CH)

( * ) Notice: Subject to any disclaimer, the term of this patent is extended or adjusted under 35 U.S.C. 154(b) by 1073 days.

This patent is subject to a terminal disclaimer.

(21) Appl. No.: 10/468,432

(22) PCT Filed: Feb. 21, 2002

(86) PCT No.: PCT/IB02/00558

§ 371 (c)(1), (2), (4) Date: Feb. 9, 2004

(87) PCT Pub. No.: WO02/065913

PCT Pub. Date: Aug. 29, 2002

(65) Prior Publication Data

US 2004/0138549 A1    Jul. 15, 2004

(51) Int. Cl.
*A61B 5/05* (2006.01)

(52) U.S. Cl. ............ 600/407; 600/408; 600/409; 600/410; 600/419; 600/420

(58) Field of Classification Search ......... 600/407–410, 600/419, 420
See application file for complete search history.

(56) References Cited

U.S. PATENT DOCUMENTS

| 5,494,655 | A  | * | 2/1996  | Rocklage et al. | 424/9.36 |
| 5,833,947 | A  | * | 11/1998 | Rocklage et al. | 424/9.36 |
| 6,277,082 | B1 | * | 8/2001  | Gambale         | 600/549 |
| 6,792,302 | B2 | * | 9/2004  | Wintermark et al. | 600/407 |
| 7,341,562 | B2 | * | 3/2008  | Pless et al.    | 600/504 |
| 7,410,634 | B2 | * | 8/2008  | Gupte et al.    | 424/9.3 |
| 2002/0090341 | A1 | * | 7/2002 | Watson et al.  | 424/9.36 |

OTHER PUBLICATIONS

Jul. 30, 2003 Non-Final Office Action, U.S. Appl. No. 09/947,058, pp. 2-3.

* cited by examiner

*Primary Examiner*—Long V Le
*Assistant Examiner*—Sanjay Cattungal
(74) *Attorney, Agent, or Firm*—Mintz, Levin, Cohn, Ferris, Glovsky and Popeo PC

(57) ABSTRACT

A method and apparatus for evaluating acute stroke patients and for determining whether a stroke patient will benefit from the use of thrombolysis therapy includes obtaining measurements of the cerebral blood flow and cerebral blood volume of the brain of a stroke patient, determining ischemic areas of the brain where the ischemic areas comprise the measurements of cerebral blood flow which are less than a first value and creating a penumbra-infarct map of the ischemic areas of the brain using the measurements. The infarct area corresponds to the area of the brain where cerebral blood volume is less than a second value. The penumbra area corresponds to the area of the brain where cerebral blood volume is greater than this second dvalue. The method also includes determining a ratio of penumbra size to the total of penumbra size and infarct size. When the ratio is greater than a predetermined value, the stroke patient is a candidate for thrombolysis therapy.

24 Claims, 18 Drawing Sheets

METHOD AND APPARATUS FOR DETERMINING TREATMENT FOR STROKE

BACKGROUND OF THE INVENTION

1. Field of the Invention

The present invention relates to determining whether thrombolysis therapy would be beneficial to an acute ischemic stroke patient, and more particularly, to methods and apparatuses for making such a determination.

2. Background of the Related Art

Ischemic strokes are the third leading cause of death after cardio-vascular diseases and cancers. In the United States alone, strokes affect over 750,000 patients each year, among whom one-third will be permanently disabled. Thus, strokes represent one of the leading causes of disability.

Viability of the cerebral tissue depends on cerebral blood flow. During a stroke, a portion of brain tissue known as the ischemic lesion is deprived of sufficient blood flow due to an arterial occlusion (blood clot). The ischemic lesion includes two parts: the infarct and the penumbra. The infarct comprises brain tissue in which blood flow is so drastically reduced that the brain cells do not recover. The penumbra surrounds the infarct and corresponds to a transitional zone in which brain cells are endangered, but not yet irreversibly damaged.

A major difference between penumbra and infarct relates to cerebral perfusion autoregulation. Complex autoregulation processes ensure both the adjustment of cerebral blood flow to local neuronal activity and cerebral blood flow stability despite changes in systemic arterial pressure. Brain vascular autoregulation notably allows for a vascular dilatation when the systemic pressure tends to lower, in order to keep a constant cerebral blood flow. This vascular dilatation leads in turn to an increased cerebral blood volume, at least in salvageable penumbra. In infarcted cerebral gray matter, autoregulation mechanisms are altered, and both cerebral blood flow and cerebral blood volume are diminished.

Early after a cerebral arterial occlusion occurs, reversible inhibition or penumbra occurs in the territory of cerebral tissue usually perfused by the affected artery. With time, irretrievable infarction, however, progressively replaces the penumbra. The replacement rate varies according to the collateral circulation level.

Thrombolysis therapy using blood clot dissolution drugs has been introduced to save ischemic but viable cerebral tissue. The application of this therapy relies on the time interval between the onset of symptomatology and the native cerebral CT findings.

However, if thrombolysis therapy is used on a patient where extensive oligemia in the territory of an occluded cerebral artery, where there is limited penumbra area, the therapy would yield little to no benefit and even increases the risk of intracranial bleeding.

SUMMARY OF THE INVENTION

Accordingly, the present invention addresses all of the above concerns and provides a method and apparatus for determining whether thrombolysis therapy would be beneficial to an acute ischemic stroke patient. The method is independent from methods currently used in perfusion-CT scans.

Using perfusion-CT examinations, the present invention provides a valuable tool in the early management of acute stroke patients, in their admission evaluation and in the choice whether to include them or not in a thrombolysis protocol.

Specifically, perfusion-CTs provide a map of cerebral blood flow, cerebral blood volume and mean transit time maps. Using a predetermined algorithm according to the present invention, the ischemic cerebral area (penumbra+infarct) is determined and mapped. After the penumbra and infarct maps are determined, they are used to calculate a potential recuperation ratio (PRR), which in effect determines whether an acute stroke patient is a candidate for thrombolysis therapy.

The present invention determines the size and location of infarct and penumbra and produces a visual image (map) of the result. These infarct and penumbra images are calculated from cerebral blood flow (CBF) and cerebral blood volume (CBV) measurements of a perfusion-CT.

The ischemic lesion (penumbra+infarct) is determined where said measurements of cerebral blood flow is a predetermined amount less than normal cerebral blood flow of an unaffected corresponding portion of the brain. Within this ischemic lesion, infarct corresponds to areas where cerebral blood volume is less than a predetermined amount and penumbra corresponds to areas where cerebral blood volume is more than this predetermined amount.

The present invention can also be used to evaluate the relative extent of the calculated infarct and penumbra to each other, thus allowing to calculate an index, called for instance potential recuperation ratio (PRR) (or Lausanne stroke index or Wintermark stroke index). This index, with adequate thresholds, can be used for determining whether an acute stroke patient is a candidate for thrombolysis therapy.

Accordingly, in a first aspect of the present invention, a method for creating a penumbra and infarct image of the brain of an acute stroke patient includes obtaining measurements of the cerebral blood flow and cerebral blood volume of the brain of an acute stroke patient and determining ischemic areas of the brain. The ischemic areas of the brain are determined where the measurements of cerebral blood flow is a predetermined first value less than normal cerebral blood flow of an unaffected corresponding portion of the brain. The method also includes creating a penumbra and infarct map comprising penumbra areas of the ischemic areas of the brain using the measurements of cerebral blood volume, where penumbra areas correspond to ischemic areas of the brain having cerebral blood volume greater than said predetermined second value. The image created according to the above method may also include infarct areas of the ischemic areas of the brain, resulting in a penumbra-infarct map of the brain. The infarct areas correspond to ischemic areas of the brain where cerebral blood volume is less than the predetermined second value.

In another aspect of the present invention, a map of the brain of a stroke patient includes penumbra areas corresponding to areas of the brain having a cerebral blood volume of greater than a predetermined value. The map may also include infarct areas corresponding to areas of the brain having a cerebral blood volume of less than the predetermined value.

In yet another aspect of the present invention, an apparatus for creating a penumbra and infarct image of the brain of an acute stroke patient includes measuring means for obtaining measurements of the cerebral blood flow and cerebral blood volume of the brain of an acute stroke patient, and determining means for determining ischemic areas of the brain. The ischemic areas are determined where the measurements of cerebral blood flow are less than a predetermined first value.

The apparatus also includes mapping means for creating a penumbra and infarct image comprising penumbra areas of the ischemic areas of the brain using the measurements. The penumbra areas correspond to areas of the brain having cerebral blood volume greater than the predetermined second value. The infarct areas correspond to areas of the brain having cerebral blood volume less than the predetermined second value.

In yet another aspect of the present invention, a computerized method for creating a penumbra and infarct image of the brain of an acute stroke patient includes storing a plurality of measurement data corresponding to the cerebral blood flow and cerebral blood volume of the pathological hemisphere of the brain of an acute stroke patient in a first database, processing measurement data to determine ischemic areas of the brain by querying the database for measurement data corresponding to cerebral blood flow being less than a first value, where a result of the query is stored as ischemic data in the database. The method also includes processing the ischemic data to determine penumbra areas of the ischemic areas, where the penumbra areas correspond to ischemic data where cerebral blood volume greater than the second value and ischemic data corresponds to the penumbra areas is stored as penumbra data. With this method, infarct areas may be included in the penumbra and infarct image, with the infarct areas corresponding to ischemic data where cerebral blood volume is less than the second value and ischemic data corresponding to the infarct areas is stored as infarct data in the database.

In yet another aspect of the present invention, a medical diagnostic apparatus for determining whether a stroke patient will benefit from the use of thrombolysis therapy includes storing means for storing a plurality of measurement data corresponding to the cerebral blood flow and cerebral blood volume of the pathological hemisphere of the brain of an acute stroke patient in a first database, processing means for:
    processing measurement data to determine ischemic areas of the brain by querying the database for measurement data corresponding to cerebral blood flow that is less than a first value, where a result of said query is stored as ischemic data in said database;
    for processing the ischemic data to determine infarct areas and penumbra areas of the ischemic areas, where infarct areas correspond to ischemic data where cerebral blood volume is less than a second value and penumbra areas correspond to ischemic data where cerebral blood volume greater than the second value. Ischemic data corresponding to infarct areas is stored as infarct data in the database and ischemic data corresponding to penumbra areas is stored as penumbra data; and
    for processing the infarct data and the penumbra data to determine a ratio that the penumbra size comprise the total of the infarct size and the penumbra size. When the ratio is greater than a predetermined third value, the stroke patient is a candidate for thrombolysis therapy.

In yet another aspect of the present invention, computer readable media having computer-executable instructions for performing the above-recited methods is provided.

In still yet another aspect of the present invention, computer readable media having stored thereon a data structure including a first field containing measurement data corresponding to the cerebral blood flow and cerebral blood volume of the pathological hemisphere of the brain of an acute stroke patient, a second field comprising ischemic data corresponding to ischemic areas of the brain, a third field comprising infarct data corresponding to infarct areas of the brain, a fourth field comprising penumbra data corresponding to penumbra areas of the brain, and a fifth field comprising ratio data comprising a ratio of penumbra size to the total of infarct size and penumbra size.

The present invention provides preferred thresholds for determining whether an acute stroke patient is a candidate for thrombolysis therapy based on infarct and penumbra maps determined by cerebral blood flow and cerebral blood volume maps of a perfusion-CT.

DETAILED DESCRIPTION OF THE PREFERRED EMBODIMENTS

For the purposes of illustration only, the imaging technique described in association with the present invention is perfusion computed tomography (perfusion CT). One skilled in the art appreciate that other imaging techniques that yield cerebral blood flow and cerebral blood volume characteristics of the brain may also be used in accordance with the scope of the present invention. These other imaging techniques include positron emission tomography (PET); single photon computed emission tomography (SPECT); stable-xenon CT, and perfusion MRI.

Computer Tomography

Figure 7:
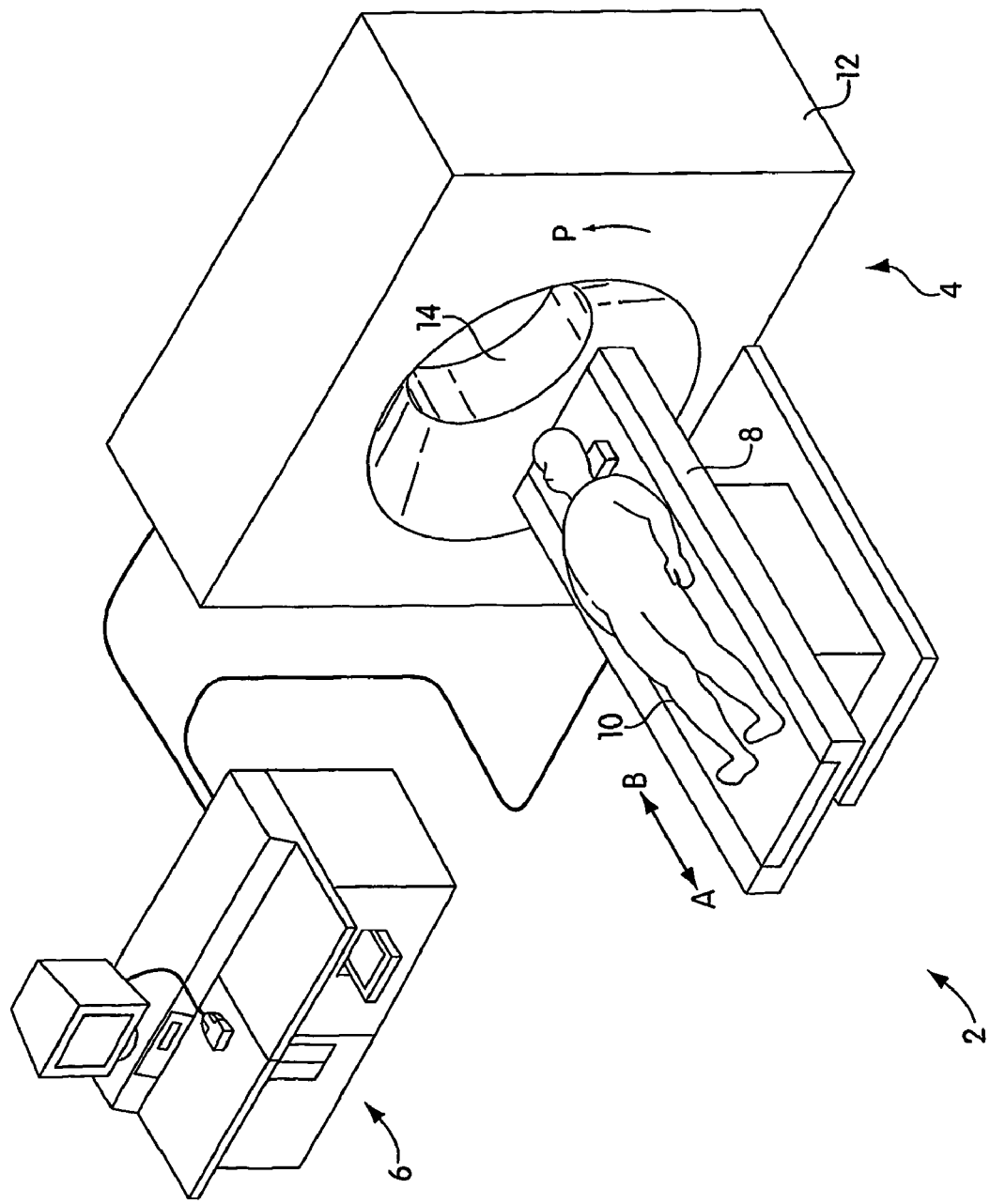
FIG. 7 illustrates a medical diagnostic apparatus according to the present invention.

As shown in FIG. 7, an x-ray computer tomography (CT) system 2 for obtaining tomographic images of a patient (such as perfusion-CT images of a patient's brain) is shown. The system includes a main x-ray CT component 4 and a control unit 6. The control unit may also function as a data-processing unit for processing image data or the like obtained by using the system.

The CT system is provided with a patient stand 8 which is arranged, on its top surface, with a movable table for placing the patient 10 thereon to be moved in directions indicated by the arrows A and B, and a gantry 12 which is formed with a cylindrical opening 14. The gantry is arranged with an x-ray tube which revolves around the cylindrical opening in a direction indicated by the arrow p, and a detector which is composed of a plurality of detector elements disposed on the circumference around the opening.

Figure 8:
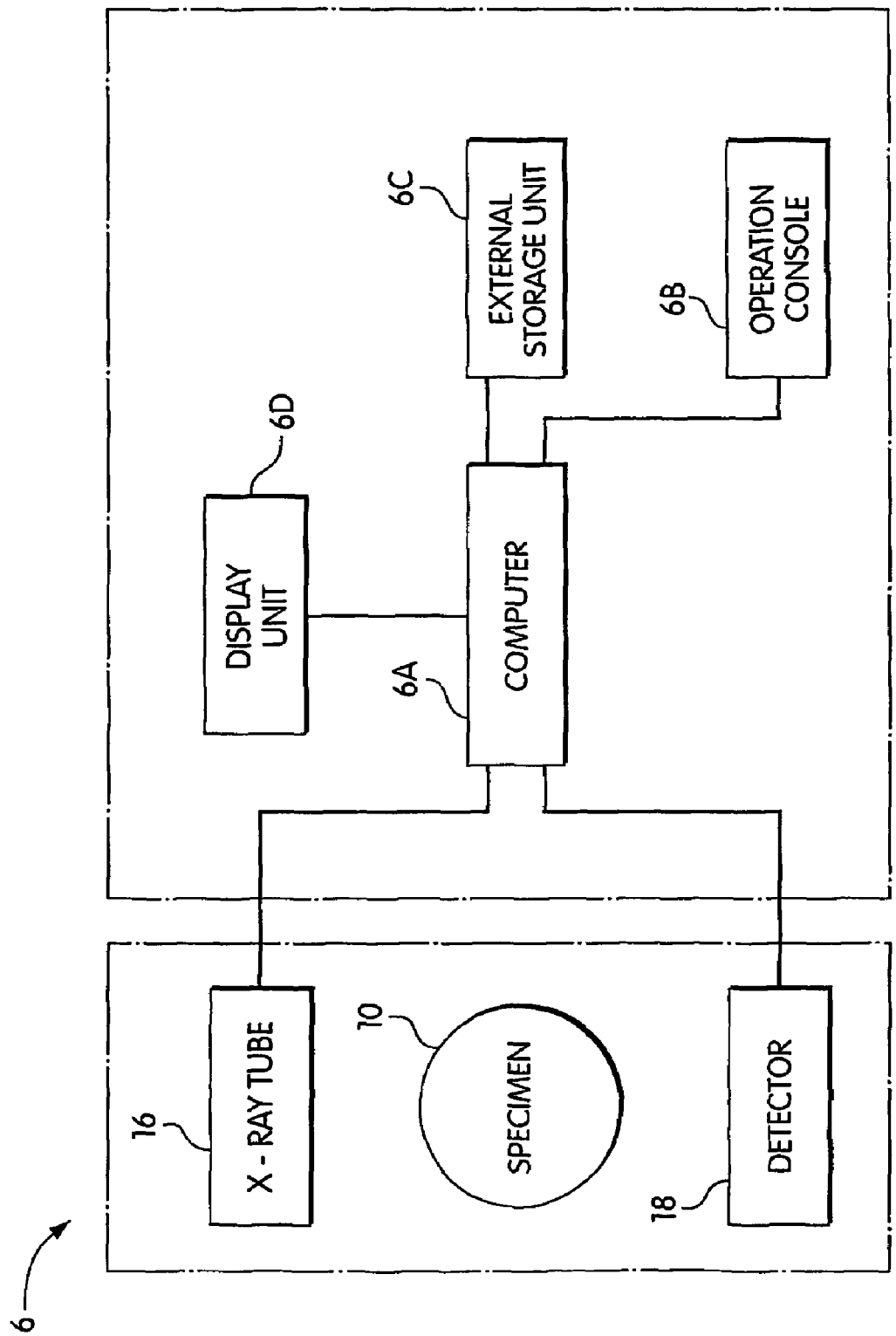
FIG. 8 illustrates a block diagram depicting the overview of the medical diagnostic apparatus shown in FIG. 7.

In FIG. 8, the control unit 6 includes a computer 6a which functions as a control unit and a processing unit. The computer is used to control the operation of the main x-ray CT system. The computer also processes the picture element data for constructing a tomographic image of an area of the patient detected by the detector disposed in the gantry to prepare, for example, the tomographic image.

The computer is further connected with an operation console 6b including a mouse and a keyboard, and external storage unit such as a magneto-optical disk unit 6c, and a display unit 6d such as a color cathode ray tube (CRT), a flat panel display, or a printing device.

The gantry includes an x-ray tube 16 and a detector 18. Each are connected to the computer/control unit for operation. As the detector detects the x-rays on an opposite side of a patient then the x-ray tube, the information is passed to the computer of the control unit so that a CT image may be formed.

Perfusion-CT is a modem imaging technique which uses a prior art method embodied in software allowing for accurate quantitative assessment of cerebral blood flow (CBF), mean transit time (MTT) and cerebral blood volume (CBV) of brain tissue.

For measuring cerebral blood flow and volume, the operation console is practically used such that a mouse pointer, which is displayed on the screen of the display unit and which is operated by using the mouse, is manipulated to click on a given display on the screen so that the process indicated by the display is executed. The CT image is represented by picture element data which is obtained by the main x-ray CT system by the aid of the computer and is displayed in a color or monochromatic illustration on the display unit. The image may also be printed out using a printing device.

Perfusion-CT examinations allow for accurate quantitative assessment of CBF and CBV. They afford definition of cerebral infarct and penumbra according to the present invention, and are easily achieved in acute stroke patients, since they involve only a sequential acquisition of cerebral CT images achieved on an axial mode during intravenous administration of iodinated contrast material. They are well tolerated and not time consuming.

Accordingly, ischemic areas of the brain are determined where the measurement of regional cerebral blood flow is less than approximately 90% that of an unaffected corresponding portion of the brain, more preferably less than approximately 75%, and most preferably less than approximately 60%.

A penumbra map comprising penumbra areas of the ischemic areas of the brain correspond to ischemic areas of the brain having cerebral blood volume between approximately 2 cc/100 grams of brain tissue and approximately 4 cc/100 grams of brain tissue.

The data from a perfusion-CT consists of contrast enhancement profiles obtained at each pixel of a CT image and relate linearly to the time-concentration curves of the contrast material. Analysis of these curves is realized according to the central size principle, which leads to an accurate result for low injection rates of iodinated contrast material.

The CBV map is inferred from a quantitative estimation of a partial averaging effect, completely absent in a reference pixel at the center of the large superior sagittal venous sinus.

The impulse function and the related mean transit time (MTT) maps are found as a result of a deconvolution of the parenchymal time-concentration curves by a reference arterial curve.

Finally, a combination of CBV and MTT at each pixel of each image map leads to a CBF value using the following equation:

$$CBF = CBV/MTT$$

In a preferred method according to the present invention, a map of the penumbra and infarcted areas of the affected brain tissue is developed using CBF and CBV maps.

Accordingly, the relative size between penumbra, when compared to the total areas of the penumbra and infarct, generally determines whether acute stroke patients will improve as a result of undergoing thrombolysis therapy. In patients with a high relative penumbra size (when compared to the total ischemic area), recanalization of the occluded cerebral artery leads to better clinical improvement.

The relative sizes between the infarct and penumbra areas is defined as an index, labeled, in the instant application, the potential recuperation ratio (PRR) (i.e., the Lausanne stroke index or Wintermark stroke index) defined by the following equation:

$$PRR = \frac{\text{penumbra size}}{\text{penumbra size} + \text{infarct size}}$$

This index generally determines whether acute stroke patients will improve as a result of undergoing intravenous thrombolysis therapy. In patients with a high PRR, recanalization of the occluded cerebral artery leads to better clinical improvement. Thus, this index can be used for determining whether an acute stroke patient is a candidate for thrombolysis therapy.

Accordingly, when the PRR is above approximately about 0.50, and more preferably above approximately 0.65, and most preferably above approximately 0.75, thrombolysis is an effective therapy for acute stroke patients, even if there is some time delay in administering the therapy. Below these values, thrombolysis therapy is generally unsuccessful, no matter what the time delay in administering the protocol. When the PRR falls short of these values, thrombolysis therapy increases the risk to an acute stroke patient of post-thrombolytic hemorrhage.

Thus, the present invention is a valuable tool in the early management of acute stroke patients, notably in creating penumbra-infarct maps of an acute stroke patient's brain, and determining whether to include a patient in a thrombolysis protocol, as shown by the following example study.

EXAMPLE

Materials & Methods

Twenty-two (22) adults (13 men, 9 women, average age of 63, ranging from 31 to 85) having an acute ischemic stroke diagnosed on the basis of clinical and native CT data were studied. Patients with a creatininaemia superior to 140 μmol/l or with an allergia to iodinated contrast material, as well as pregnant patients, were ruled out of the study. Patients' characteristics, exact location of the ischemic stroke, as well as inclusion or not in a thrombolysis protocol and recanalization of the occluded cerebral artery, are summarized in Table 1 as follows:

TABLE 1

Characteristics of the Twenty-two Patients with an Acute Stroke
Who Underwent Both Admission Perfusion-CT and Delayed MR

| Patient N° | Age [years] | Sex | Exact Location of the ischemic Stroke on the Diffusion-MR | Thrombolysis | Recanalizatio of the occluded cerebral artery |
|---|---|---|---|---|---|
| 1 | 68 | M | superficial posterior left MCA | no | yes |
| 2 | 54 | M | left MCA | yes | yes |
| 3 (†) | 84 | F | superficial and deep left MCA | yes | yes |
| 4 | 51 | F | superficial left MCA stroke | no | yes |
| 5 | 51 | F | deep posterior right MCA | no | yes |
| 6 | 76 | F | superficial anterior right MCA | no | yes |
| 7 | 46 | F | posterior right MCA | no | no |
| 8 | 78 | M | basilar artery | yes | yes |
| 9 | 71 | M | superficial posterior left MCA | yes | yes |
| 10 | 71 | M | posterior left MCA | yes | yes |
| 11 | 61 | M | superficial right MCA | yes | no |
| 12 | 43 | F | left MCA | no | no |
| 13 | 31 | M | anterior right MCA | no | no |
| 14 | 50 | M | posterior left MCA | no | yes |
| 15 (FIG. 1) | 74 | F | anterior right MCA | no | yes |
| 16 | 85 | F | superficial anterior left MCA | no | no |
| 17 | 68 | M | superficial left MCA | yes | yes |
| 18 | 75 | M | right MCA | yes | no |
| 19 | 33 | M | right MCA | no | no |
| 20 | 80 | F | right MCA | no | yes |
| 21 | 61 | M | posterior right MCA | no | yes |
| 22 (FIG. 2) | 83 | M | left MCA | no | no |

The non-enhanced baseline cerebral CT was immediately followed by a perfusion CT, as part of the initial survey of acute stroke patients performed. In 12 patients, the admission cerebral CT survey ended with a cerebral and cervical angio-CT.

Among the 22 patients, 8 were eligible for an intravenous thrombolytic therapy, meaning that time delay was adequate, stroke size was inferior to one third of the MCA territory on the native cerebral CT and that there were no contra-indications.

Thrombolysis began 2.7±1.0 hours after the onset of symptomatology. No complications (notably no hemorrhages) happened in the eight thrombolyzed patients. However, one patient died 15 days after the onset of symptomatology from septicemia consecutive to pulmonary infection.

After a delay of 3.3±1.5 days (4.0±1.3 in the thrombolysis group and 3.0±1.6 hours in the non-thrombolysis group; p value=0.209), a MR examination was obtained in each of the 22 patients, including T2- and diffusion-weighted series, as well as cerebral and cervical angio-MR.

Besides the admission CT and the delayed MR, two patients underwent a second cerebral CT survey in the time interval between the former two (2.0±1.0 days after the onset of symptomatology). Sequential perfusion-CT and MR examinations in two of these patients were used to demonstrate the evolution of penumbra over time, with and without arterial recanalization (see FIGS. 1 and 2).

Time delays between the onset of symptomatology and admission to the emergency room, the perfusion-CT examination, the beginning of the thrombolysis, as well as the delayed MR were recorded.

Permeability of cerebral and cervical vessels was assessed on the admission angio-CT and the delayed angio-MR.

The NIHSS, the Barthel index and the modified Rankin scale were evaluated in twenty-one patients (one patient in the thrombolysis group died 15 days after the symptomatology onset), both on admission and after a 2.2±0.8 month-time delay (2.5±0.9 months in the thrombolysis group and 2.1±0.7 months in the nonthrombolysis group; p=0.298). The improvement of NIHSS between admission at this time delay was calculated and considered as a witness of the evolution of the clinical condition.

Imaging Techniques

Perfusion CT examinations consisted in two series obtained at a 5-minute time-interval from each other. Each series involved 40 successive cerebral CT sections achieved every second on a cine mode, during intravenous administration of iodinated contrast material. Total acquisition time was 40 seconds. Acquisition parameters included for each of the two series: 80 kVP and 100 mA. For each series, CT scanning was initiated 5 seconds after intravenous administration of 50 cc of iohexol—concentration of 300 mg/cc iodine—in an antecubital vein by means of a power injector at a rate of 5 cc per second. The delay before injection of the contrast material allowed for the acquisition of baseline images without contrast enhancement. Multidetector-array technology allowed acquisition of two adjacent 10-mm sections for each series. The performed two perfusion-CT series thus allowed to acquire data regarding four adjacent 10-mm cerebral CT sections. The four studied cerebral sections were chosen above the orbits to protect lenses, going through the basal nuclei and above them towards the vertex.

Considering acquisition of four adjacent 10-mm sections at 80 kVp, the measured normalized and weighted computed tomography dose index (nCTDIw) amounts to 0.112 mGy/mAs. Supposing a perfusion CT protocol of 40 successive slices obtained on an axial mode at 100 mA and with regard to the geometry of radiation delivery (dose efficiency of 86%, for instance), the resultant radiation dose amounts to 368 mGy. Regarding the stochastic effect of radiations, these calculated doses must be redistributed on the whole cerebral size. Since a 40-mm thickness relates approximately to a fifth of the cerebral size, the brain absorbed dose is 77 mGy. Considering a weighting factor of 0.0023 mSv/(mGy×cm) for the brain, the cerebral effective dose is 3.4 mSv, which is quite equivalent to the reference dose level for a standard cerebral CT examination (2.5 mSv).

The cerebral and cervical angio-CT was realized with the following protocol: 120 kVp, 240 mAs; slice thickness 2.5 mm, slice acquisition interval 2 mm; pitch=1.5:1; intravenous administration of 40 cc of iodinated contrast material at a rate of 3 cc per second, acquisition delay=10 seconds. Data acquisition was achieved from the origin of the aortic arch branch vessels to the Willis' polygon.

After a delay of 3.3±1.5 days (4.0±1.3 in the thrombolysis group and 3.0±1.6 hours in the non-thrombolysis group; p value=0.209), a MR examination was obtained in each of the 22 patients on a 1.51 MR unit. This MR examination included spin-echo T2-weighted series and trace diffusion-weighted series (echoplanar spin-echo, TR=5,000 msec, IE=100 msec, b=1,000, 20 5-mm-thick slices with a 1.5-mm gap, matrix size=128×128). Angio-MR was performed with a time-of-flight multislab 3D FLASH technique for cerebral and cervical vessels. A 3D FISP technique during the intravenous administration of a bolus of gadolinium was also used for cervical vessels.

Data Processing

The perfusion-CT data were analyzed by a perfusion analysis software to create parametric maps of CBV, MTT and CBF. Perfusion CT and MR were then transferred to a workstation. Penumbra and infarct maps were calculated in applying the concepts according to the present invention, and in taking the lateralization of clinical symptomatology into consideration.

The ischemic cerebral area (penumbra+infarct) was chosen to include cerebral pixels with a CBF lowering superior to 34% when compared with the symmetrical region in the cerebral hemisphere defined as healthy according to the clinical symptomatology. In this selection area, 2.5 cc per 100 grams was chosen as a threshold for CBV values. Within the selection area, pixels with CBV superior to 2.5 cc per 100 grams were attributed to the penumbra, whereas pixels with CBV inferior to 2.5 cc per 100 grams were included in the infarct. The resultant cerebral penumbra and infarct maps were combined in a prognostic map.

Four among the diffusion-weighted MR cerebral sections in the diffusion-weighted sequence were selected as being the closest to the chosen perfusion-CT sections, knowing that the two examination techniques forbade an exact correspondence between CT and MR selected sections.

The infarcted cerebral area on the diffusion-weighted MR images was defined by using an intensity threshold, the infarcted cerebral area including the pixels with an intensity value above the threshold. The latter was chosen in order to rule out contralateral hemisphere and choroidal plexi from the infarcted area, the stroke being unilateral in all of the twenty-two patients.

Data Analysis

Final results included a perfusion-CT penumbra map, a perfusion-CT infarct map and a diffusion-weighted MR infarct map, and these for each of the four sections obtained in each of the twenty-two examined patients. The examined diffusion-weighted MR sections were selected at approximately the same level as the perfusion-CT sections. These sections could not be exactly the same, CT and MR examinations being obtained within a few day interval.

(1) The perfusion-CT infarct and penumbra maps were first used to measure the size of the predicted infarcted area in $cm^2$. The size of the definite infarcted area was measured on the corresponding diffusion-weighted MR sections and regarded as the gold standard for the statistical analysis. Linear regression analysis and bilateral T-tests for matched variables were used to compare the size of the perfusion-CT and diffusion-weighted MR infarcted areas on the corresponding sections. Significance was stated at p values lower than 0.05.

(2) The perfusion-CT penumbra and infarct maps were used to calculate a potential recuperation ratio (PRR) according the PRR equation:

$$PRR = \frac{\text{penumbra size}}{\text{penumbra size + infarct size}}$$

For each patient, only one average PRR was calculated from the four imaged cerebral levels.

The correlation between the admission NIHSS and the size of the ischemic cerebral area on the admission perfusion-CT, the correlation between the delayed NIHSS, the Barthel index as well as the modified Rankin score and the size of the infarct on the delayed diffusion-weighted MR, as well as the correlation between the NIHSS improvement and the PRR, were evaluated through linear regression analysis.

Results

Time Delays

Mean time from the onset of symptomatology to the emergency room admission amounted to 3.9±2.1 hours (2.0±0.9 in the thrombolysis group and 4.9±2.8 hours in the non-thrombolysis group; p value=0.009), while mean time from the onset of symptomatology to the perfusion-CT scanning was 4.6±2.4 hours (2.3±1.0 in the thrombolysis group and 5.9±3.2 hours in the non-thrombolysis group; p value=0.010). Perfusion-CT examinations were well tolerated by all 22 patients and involved only a 10-minute additional delay for the admission cerebral CT survey.

Arterial Recanalization or Persistent Arterial Occlusion

In 8 cases out of 12 who underwent admission angio-CT, all demonstrated an occluded cerebral artery. In 4 patients, the occluded cerebral artery responsible for the stroke had already repermeabilized at the time of the angio-CT, correlating with an improvement of the clinical condition.

The delayed angio-MR performed in the 22 patients of the series allowed the evaluation of a potential recanalization of the occluded cerebral artery, either spontaneously or as the result of thrombolytic therapy (table 2). In 14 patients (2 patients in the thrombolysis group and 6 patients in the non-thrombolysis group), angio-MR demonstrated a persistence of the arterial occlusion. Out of the 8 patients with an occluded artery on the admission angio-CT, 5 showed a recanalization on the delayed angio-MR, whereas 3 demonstrated persistent occlusion. The repermeabilized artery displayed in 4 patients on the admission angio-CT remained permeable on the delayed angio-MR.

Correlation Between Admission Perfusion-CT and Delayed Diffusion-Weighted MR Perfusion-CT data defined CBV, MTT and CBF maps. From the latter infarct and penumbra maps were determined, easily calculable for each patient of the series.

In patients with a persistent occluded cerebral artery on the delayed angio-MR (FIGS. 1 and 3), the average size of the combined perfusion-CT infarct and penumbra areas was $37.8 \pm 15.5$ cm2, whereas the corresponding value on diffusion-weighted MR series was $39.7 \pm 17.3$ cm$^2$. No significant statistical difference (p value=0.332) could be observed between these significantly correlated values ($_{diffusion-MR}$infarct=$3.659 + 0.861 \times _{perfusion-CT}$infarct+penumbra; r$^2$=0.918).

In all patients with a repermeabilized cerebral artery on the delayed anglo-MR (FIGS. 2 and 4), the size of the final cerebral infarct defined on the delayed diffusion-weighted MR ranged between the admission perfusion-CT size of the cerebral infarct and the total ischemic area.

In both cases, the shape of the infarct or infarct-penumbra areas showed subjective good agreement on perfusion-CT as well as diffusion-weighted MR images, as demonstrated in FIGS. 1 and 2.

Regarding the comparison between admission perfusion-CT and delayed diffusion-weighted MR, the results underline the excellent prognostic value of admission perfusion CT regarding the final size of cerebral infarct, defined on reference diffusion-weighted MR sequences. As explained above, diffusion-weighted MR has been demonstrated to accurately delineate the cerebral infarct. In order to avoid pitfalls related to biphasic phenomenons, a diffusion-weighted MR achieved $3.3 \pm 1.5$ days after stroke was used as a reference.

Eight of the twenty two acute stroke patients showed persistent arterial occlusion. Two of them underwent unsuccessful thrombolytic therapy. In these patients with persistent arterial occlusion (FIG. 4), the size of the combined cerebral infarct and penumbra areas on the admission perfusion-CT closely correlated with the size of the cerebral infarct on the delayed MR. No statistical difference could be observed.

The penumbra defined on the admission perfusion-CT gradually evolved towards infarct: the whole cerebral ischemic area, first reversible, became irretrievable infarct with time, due to the prolongation of the arterial occlusion (FIG. 2), thus explaining the observed correlation.

Fourteen of the twenty-two acute stroke patients showed repermeabilization of the occluded cerebral artery. Six of them underwent thrombolytic therapy, whereas in eight, the recanalization was spontaneous. In the patients with recanalization of the occluded cerebral artery (FIG. 3), the size of the final cerebral infarct defined on the delayed diffusion-weighted MR always ranged between the admission perfusion-CT size of the cerebral infarct and the total ischemic area. More precisely, its average was located at 22.6% of the range defined by the admission perfusion-CT size of the cerebral infarct and the total ischemic area. This is likely related to an evolution of the infarct over the penumbra as defined on the admission perfusion-CT until arterial recanalization, followed by a recovery of the remaining penumbra (FIG. 1).

The 22.6%-average location of the final size infarct indicates that, when recanalization has to occur, it generally happens early in the chronological course of the stroke.

Correlation Between Perfusion-CT and Clinical Condition

Figure 5:
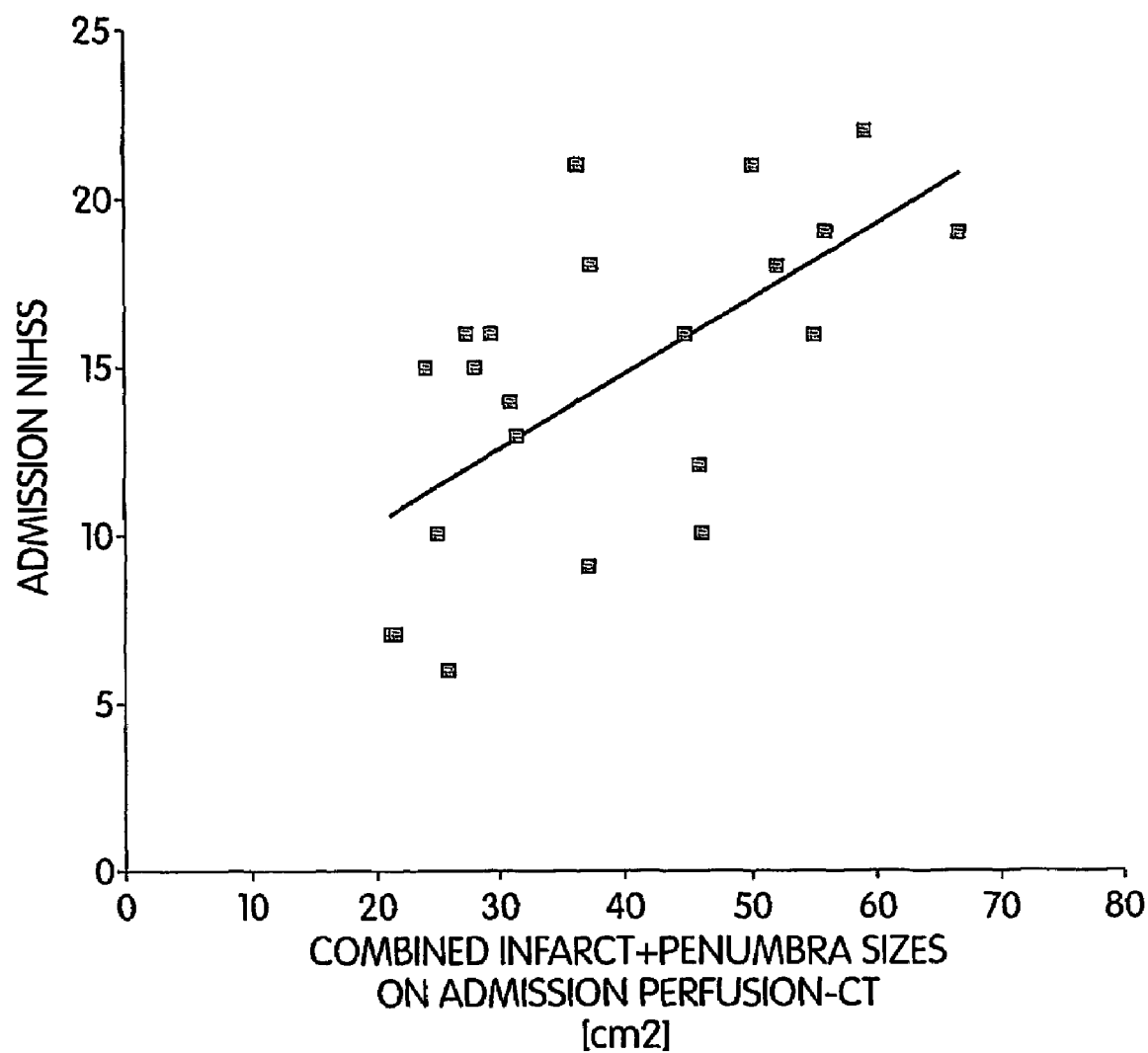
FIG. 5 illustrates the correlation between the admission NIHSS and the combined infarct-penumbra size on the admission perfusion-CT.

The admission NIHSS increased concomitantly with the initial size of the combined infarct and penumbra areas on the admission perfusion-CT ($_{admission}$NIHSS=$26.815 + 4.504 \times _{perfusion-CT}$infarct+penumbra; r$^2$=0.627) (FIG. 5).

On the other hand, no significant correlation could be found between the size of the final cerebral infarct as defined on the delayed diffusion-weighted MR and the delayed NIHSS (r$^2$=0.408), the Barthel index (r2=0.430) and the modified Rankin score (r$^2$=0.302).

Finally, the potential recuperation ratio (PRR) was distributed as follows and is exhaustively described in Table 2:

TABLE 2

Overview of the NIHSS Evolution Over a 2.2 ± 0.8-Month Period and of the Potential Recuperation Ratio (PRR) in the Series of Twenty-Two Patients

|  | Thrombolysis | No thrombolysis |
| --- | --- | --- |
| Arterial recanalization | 5 patients (+ 1 death) delay to hospital admission = 2.4 ± 1.2 hours delay to thrombolysis = 3.1 ± 1.2 hours PRR = 81% ± 16% NIHSS improvement = 74% ± 20% | 8 patients delay to hospital admission = 4.5 ± 3.5 hours PRR = 71% ± 11% NIHSS improvement = 62% ± 20% |
| No arterial recanalization | 2 patients delay to hospital admission = 2.0 ± 0.0 hours delay to thrombolysis = 2.8 ± 0.4 hours PRR = 69% ± 15% NIHSS improvement = 55% ± 19% | 6 patient delay to hospital admission = 5.8 ± 4.0 hours PRR = 60% ± 12% NIHSS improvement = 42% ± 12% |

In 6 patients, no thrombolysis was performed and the delayed angio-MR revealed a persistent occluded cerebral artery. In these patients, an average NIHSS improvement of 42%±12% was observed. The PRR was 60%±12%.

In 8 patients, no thrombolysis was achieved, and an arterial recanalization was diagnosed on the delayed angio-MR. The average NIHSS improvement was 62%±20%: the PRR was 71%±11%.

In 6 patients, thrombolysis was performed and successful. In these patients, an average NIHSS improvement of 74%±20% was observed and the PRR amounted to 81%±16%.

In 2 patients, thrombolysis was performed, but allowed for no arterial repermeabitization. In these patients, the average NIHSS improvement was 55%±19% and the PRR amounted to 69%±15%.

Among the patients who underwent thrombolysis, those with persistent occluded cerebral artery tended to show a lower NIHSS improvement of 69%±15% (p value=0.354). This was associated with a trend towards a lower PAR (p value=0.297).

Figure 6:
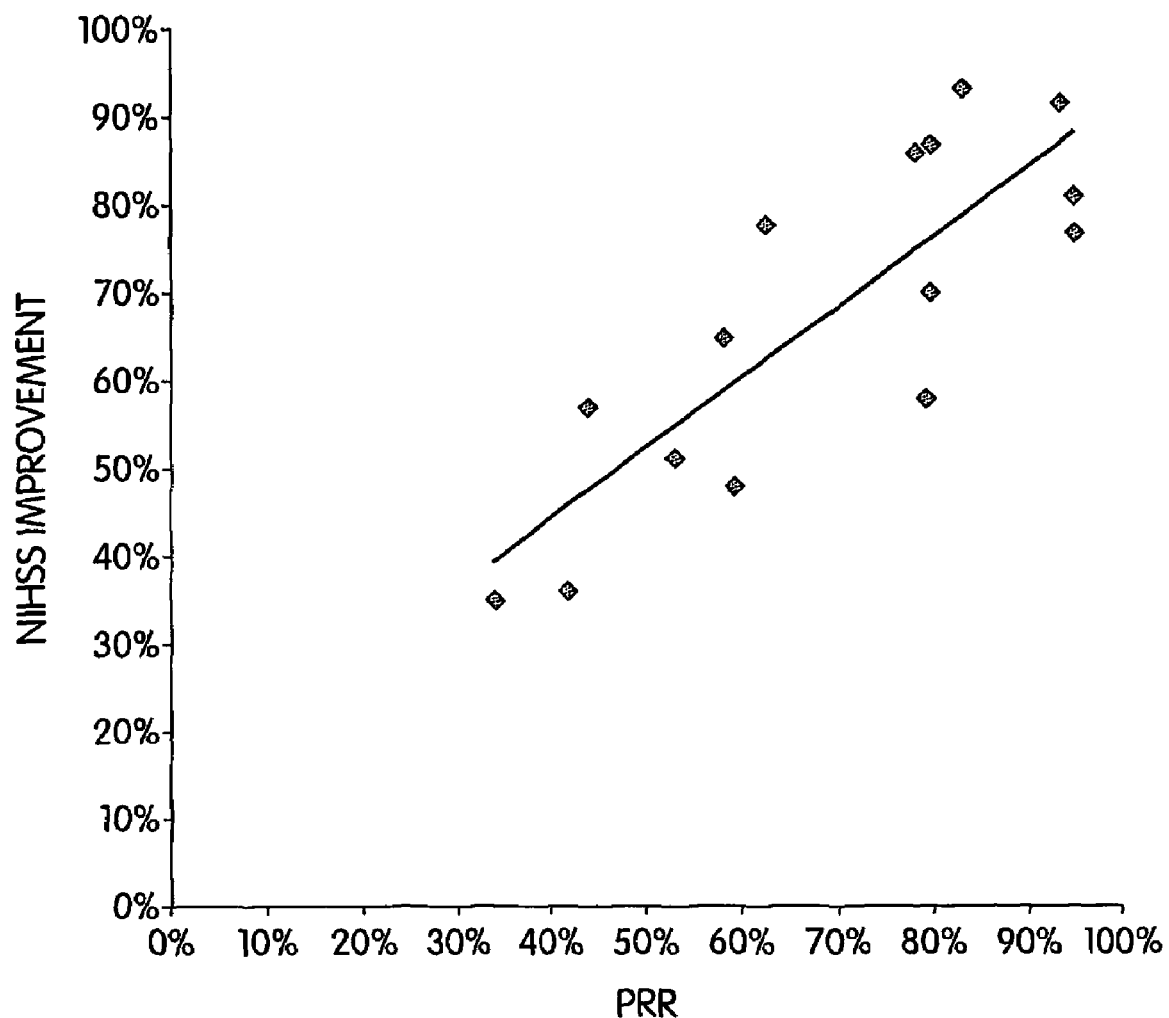
FIG. 6 illustrates the correlation between the PRR and the NIHSS improvement in acute stroke patients with arterial recanalization.

In patients with recanalization of the occluded cerebral artery, either spontaneous or consecutive to thrombolysis, there was a strong correlation between the PRR and the improvement of the NIHSS evaluated on admission and after a 2.2±0.8-month time delay (NIHSS improvement=0.108±0.863×$_{perfusion-CT}$PRR; $r^2$=0.831; FIG. 6

In patients with a persistent occluded cerebral artery, whether spontaneous or consecutive to thrombolysis, the NIHSS improvement was globally poorer (45%±15% in the persistent occlusion group versus 67%±20% in the recanalization group, p value=0.059). The PRR also tended to be lower in the persistent occlusion group than in the recanalization group (71%±11% versus 60%±12%, p value=0.005).

The method to calculate cerebral penumbra and infarct maps from the CBF and CBV maps inferred from perfusion-CT data analysis relies i) upon reported rCBF threshold of ischemia and ii) upon the persisting or alterated autoregulation mechanisms. In the penumbra area, the CBV is superior to 2.5 cc per 100 grams, whereas, in the infarcted area, the CBF is inferior to 2.5 cc per 100 grams.

In the first part of the study, a correlation between the ischemic cerebral areas displayed by two imaging techniques was found, a reference one (diffusion-weighted MR) and one to be validated (perfusion-CT). In the second part of the study, an evaluation of the clinical relevance of perfusion-CT examinations performed on admission in acute stroke patients. As witness of the clinical condition of the acute stroke patient, three clinical scores were chosen, the NIHSS, the Barthel index and the modified Rankin scale, which proved relevant. Moreover, the evolution of the NIHSS between the admission and after a 2.2±8-month delay was examined.

A good correlation between the admission NIHSS and the initial size of the combined cerebral infarct and penumbra areas defined on the admission perfusion-CT was identified, as shown on FIG. 5, and, on the other hand, a poor correlation between the delayed diffusion-weighted MR size of the cerebral infarct and the various clinical scores. The more likely explanation for the lesser correlation of the diffusion-weighted MR lesion sizes with delayed clinical scores is that a 3.3±1.5-day MR examination was being compared with 2.2±0.8-month clinical scores, rather than with simultaneous clinical scores, and that neural repair and neuroplasticity allow improvement to occur variably across different patients by later clinical timepoints.

Finally, a new parameter, called potential recuperation (PRR) was determined, which relates to the relative size of penumbra and infarct, with respect to the NIHSS improvement between admission and a 2.2±0.8-month time delay (see Table 2).

In fourteen patients, no thrombolysis was performed. In eight of them, spontaneous fragmentation of the thrombus with recanalization of the occluded cerebral artery occurred, as demonstrated by the delayed angio-MR. In six of them, no arterial recanalization occurred. In the second patient group, the clinical evolution tended to be poorer, reflected by a trend to lower both NIHSS improvement and PRR.

Thrombolysis was achieved in eight patients, allowing recanalization of the arterial thrombus and rescuing the penumbra in six of them 10, reflected by a high NIHSS improvement of 74%±20%. In two patients, thrombolysis was unsuccessful, reflected by a NIHSS improvement of only 55%±19%. PRR tended to be lower in the second group than in the first.

In patients with recanalization of the occluded cerebral artery, whether spontaneous or consecutive to thrombolysis, there was a strong correlation between the PRR and the improvement of the NIHSS evaluated on admission and after a 2.2±0.8-month delay (FIG. 7). In these patients indeed, recanalization, whether spontaneous or consecutive to thrombolysis, allowed to rescue the penumbra, with a subsequent and proportional improvement of the clinical condition.

In patients with a persistent occluded cerebral artery, the cerebral infarct evolved with time over the penumbra and finally completely replaced it, as reflected by a globally poorer NIHSS improvement.

Detailed Description of The Computer Tomography Images

FIG. 1*a-f*. Progression of infarct over penumbra in case of persistent cerebral arterial occlusion. 83-year-old male patient with suspected anterior left sylvian artery stroke a Non-contrast cerebral CT (first line) obtained on admission, 7 hours after symptomatology onset, demonstrates an old right frontal lesion, as well as a slight left insula ribbon sign, whereas more sensitive perfusion-CT prognostic map (fifth line) identifies a deep left MCA ischemia, with an infarct (red) component located on the left semi-oval center and a penumbra (green) lying on the left internal capsula, insula and parietal operculum. Mean transit time (MTT) (second line) and cerebral blood flow (CBF) (third line) are increased and lowered, respectively, in both infarct and penumbra, whereas cerebral blood volume (CBV) (fourth line) is lowered in infarct, and preserved or increased in penumbra, because of autoregulation processes. b Admission angio-CT maximum intensity projection (MIP) displays the occluded left MCA responsible for the reported cerebral ischemia. No thrombolysis was performed due to the time delay. Worsening of the clinical condition justified the performance of c a second CT 28 hours after the first. The native cerebral CT (first line) demonstrates a cerebral infarct in the exact location reported on the first perfusion-CT. The perfusion-CT prognostic map (fifth line) discloses an almost complete replacement of the first perfusion-CT penumbra (green) by infarct (red). d The second angio-CT explains this findings by a persistent occlusion of the left MCA. e 6 days after admission, diffusion-weighted MR demonstrates the cerebral infarct, which closely correlates with the one described on the second perfusion-CT prognostic map. The persistent occlusion of the left MCA was confirmed by f angio-MR.

FIG. 2*a-f*. Recovery of the penumbra in case of cerebral arterial recanalization. 74-year-old female patient with anterior right sylvian artery stroke suspected on the basis of the physical examination 5 hours after symptomatology onset. a Native cerebral CT obtained at the same time (first line) demonstrates a subtle cortico-medullar de-differentiation on the head of the right caudate nucleus, whereas more sensitive perfusion-CT prognostic map (second line) clearly identifies a deep right MCA ischemia, with an infarct (red) component located on the head of the right caudate nucleus and a penumbra (green) lying on the right internal capsula and lenticulate nucleus. b Admission angio-CT maximum intensity projection (MIP) displays the occluded right MCA responsible for the reported cerebral ischemia. No thrombolysis was performed due to the time delay. The spontaneous evolution of the clinical condition was favorable, but occurring of a generalized seizure 7 hours after the first CT justified the performance of c a second CT to rule out a reperfusion hemorrhage. The native cerebral CT (first line) does not display any extension of the ischemic territory depicted on a. The perfusion-CT prognostic map (second line) shows discloses a limited progression of the infarct (red) over the first perfusion-CT penumbra, whereas the latter (green) has mostly resolved. d The second angio-CT explains these findings by a right MCA recanalization. The latter occurred some time after the first CT, this time delay allowing for the observed progression of the infarct. Immediately after the recanalization, the infarct progression over the penumbra was stopped and the salvageable ischemic cerebral tissue of the penumbra could recover. e 3 days after admission, diffusion-weighted MR demonstrates the residual irretrievable infarct, which closely correlates with the one described on the second perfusion-CT prognostic map. f Right MCA recanalization was again demonstrated by delayed angio-MR.

Figure 1A:
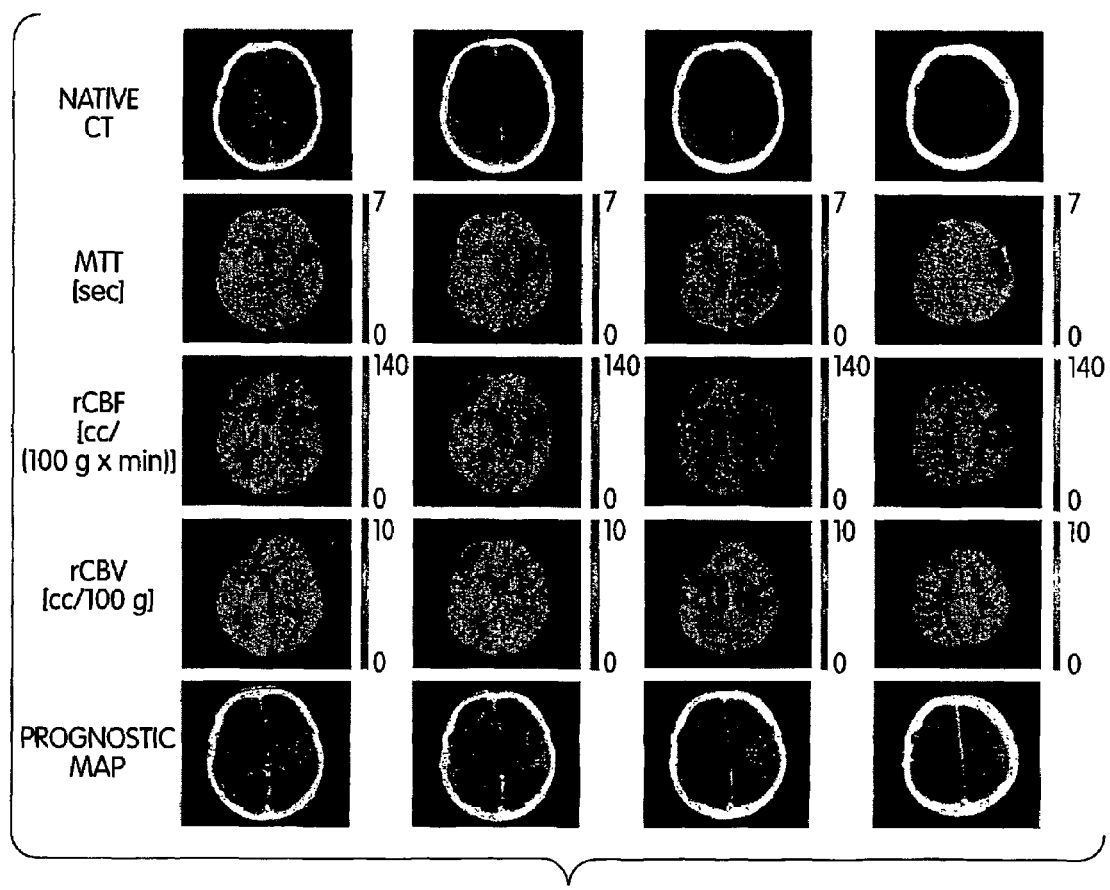
FIGS. 1a-f illustrate the progression of infarct over penumbra in case of persistent cerebral arterial occlusion.
Figure 1B:
Figure 1C:
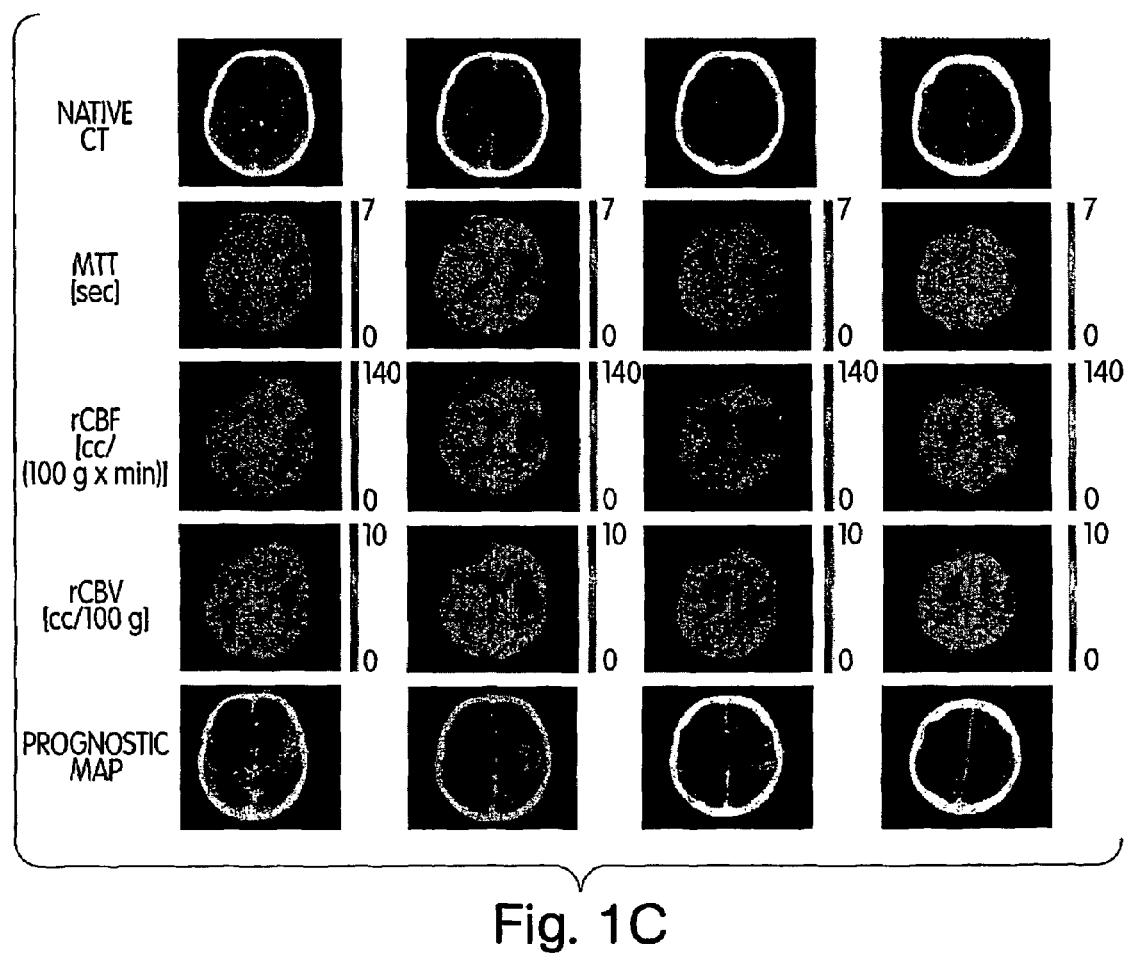
Figure 1D:
Figure 1E:
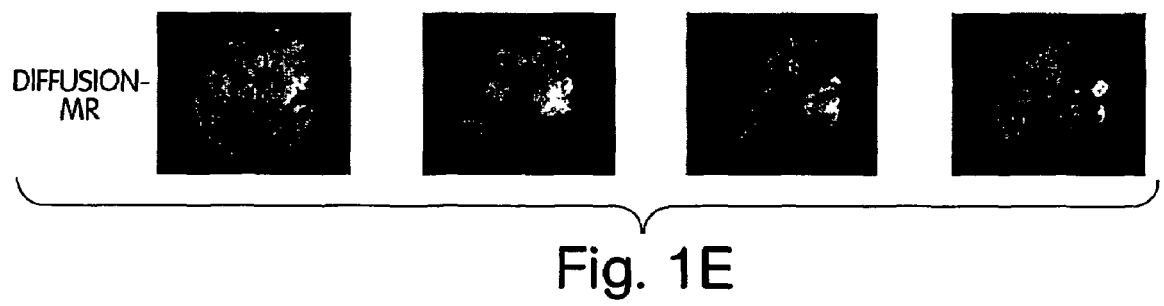
Figure 1F:
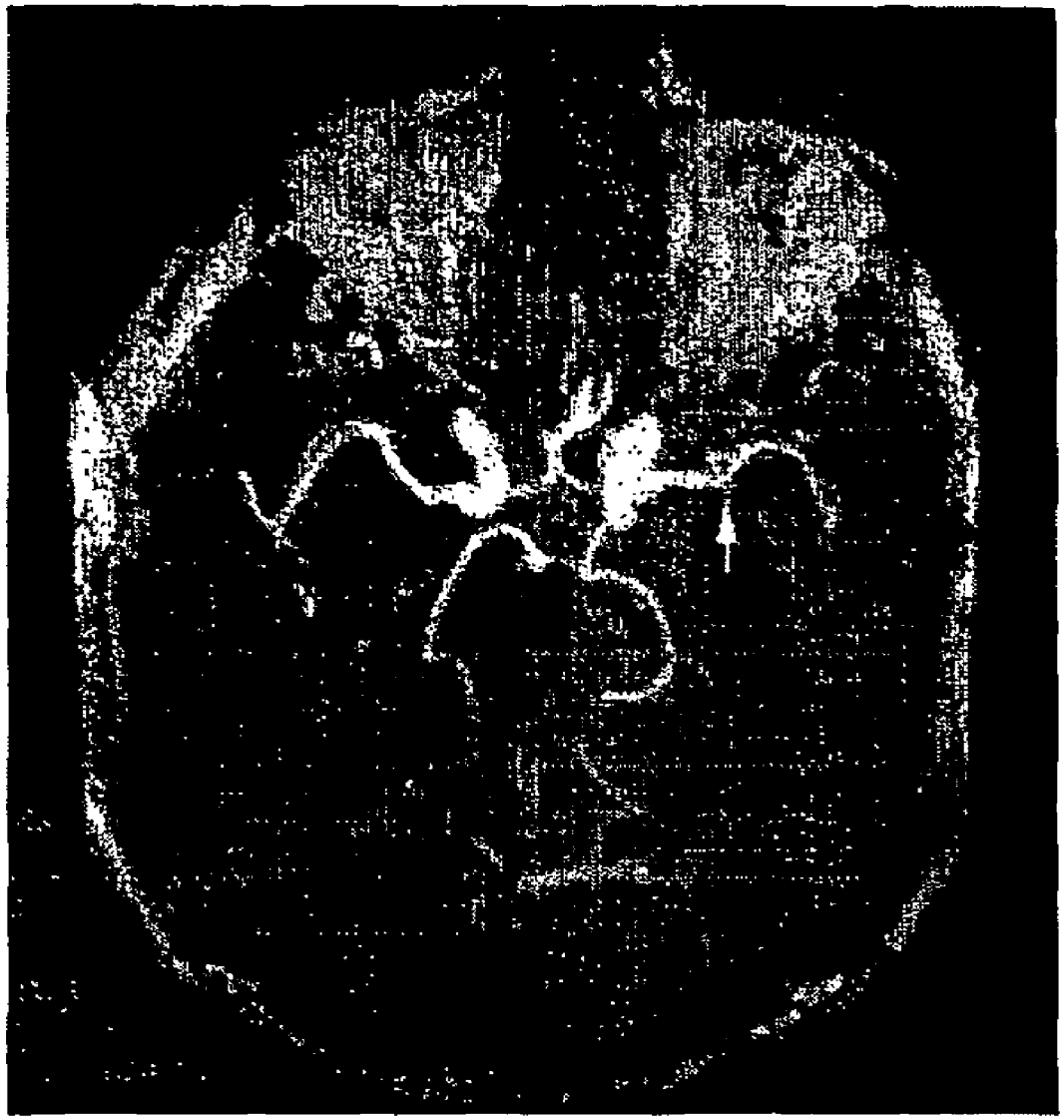
Figure 2A:
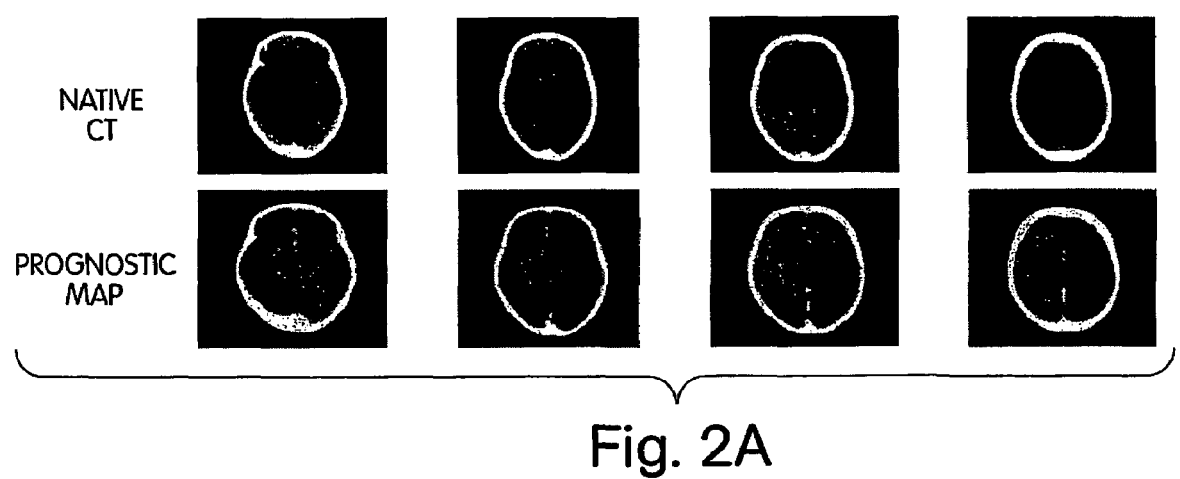
FIG. 2a-f illustrate the recovery of the penumbra in case of cerebral arterial recanalization.
Figure 2B:
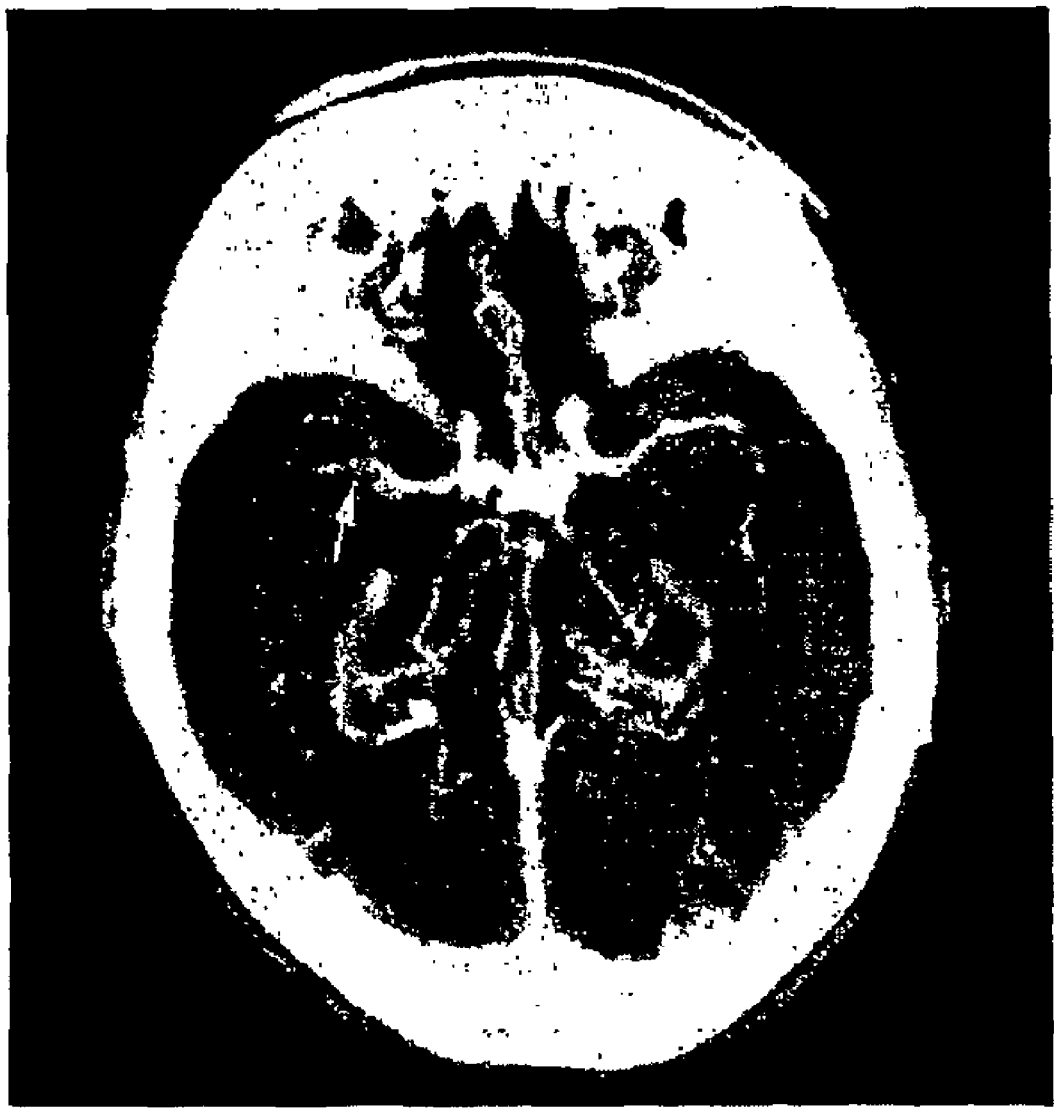
Figure 2C:
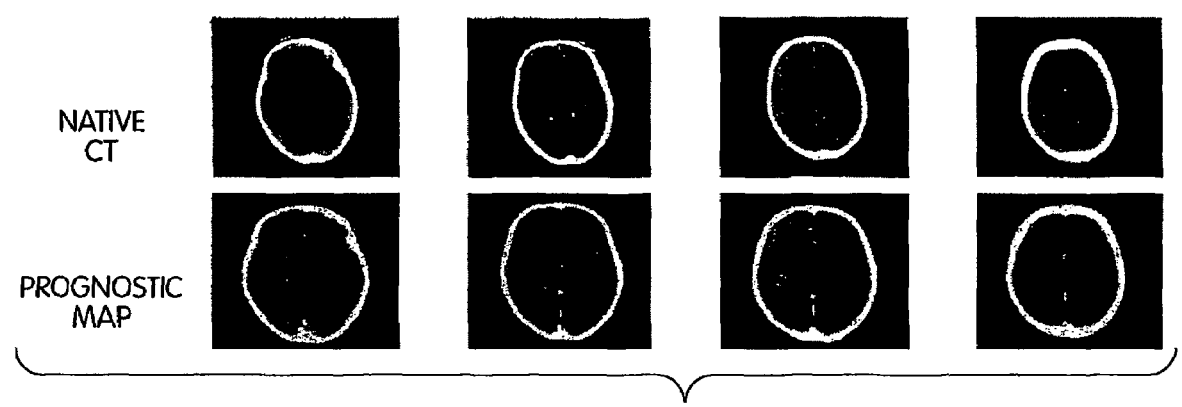
Figure 2D:
Figure 2E:
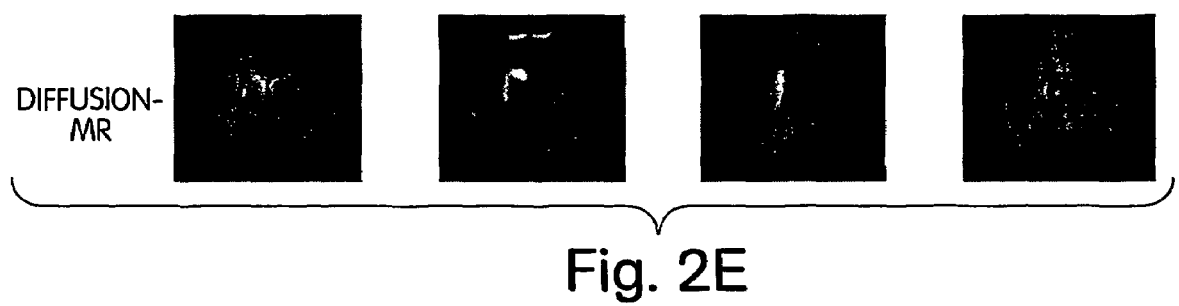
Figure 2F:
Figure 3:
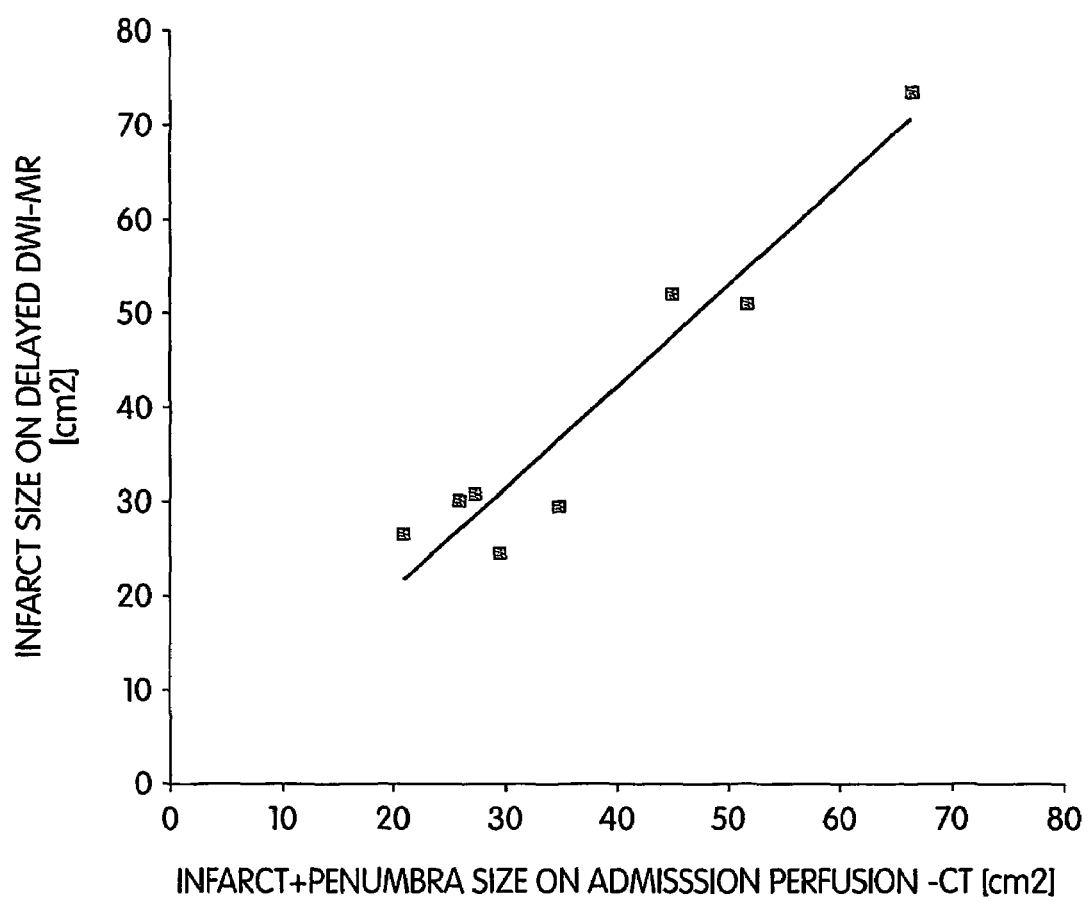
FIG. 3 illustrates the relation between the admission perfusion-CT and delayed diffusion-weighted MR size of ischernic areas in acute stroke patients without arterial recanalization.

FIG. 3. Relation between the admission perfusion-CT and delayed diffusion-weighted MR size of ischemic areas in acute stroke patients without arterial recanalization. In patients with persistent arterial occlusion, the delayed diffusion-weighted MR size of the cerebral infarct strongly correlated ($_{diffusion-MR}$ifarct=3.659±0.861×$_{prefusion-CT}$infarct+penumbra; $r^2$ =0.918) and showed no statistically significant difference (p=0.332) with the admission perfusion-CT size of the total ischemic area. In these patients indeed, the penumbra defined on the admission perfusion-CT gradually evolved towards infarct: the whole cerebral ischemic area became irretrievable infarct with time, due to the prolongation of the arterial occlusion, thus explaining the observed distribution.

Figure 4:
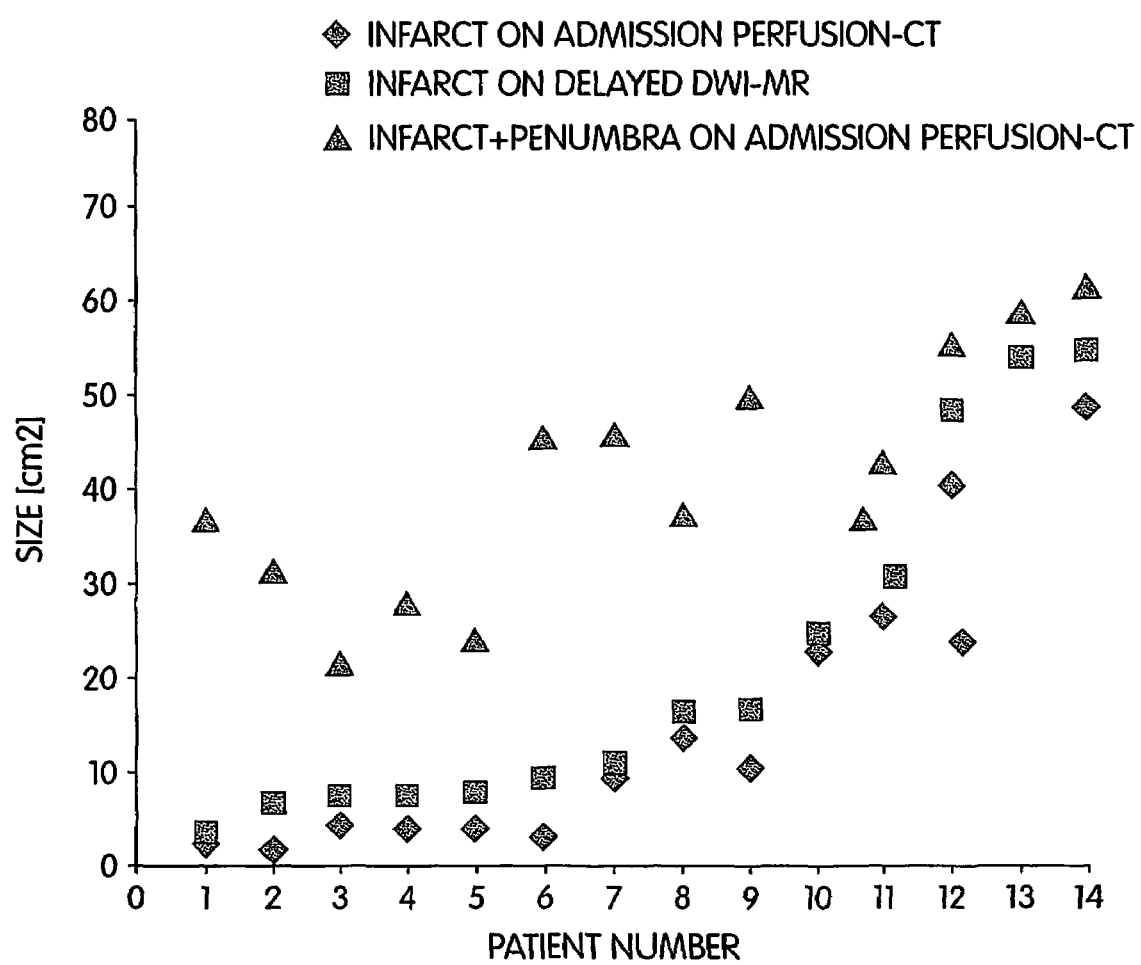
FIG. 4 illustrates the correlation between the admission perfusion-CT and delayed diffusion-weighted MR size of ischernic areas in acute stroke patients with arterial recanalization.

FIG. 4. Correlation between the admission perfusion-CT and delayed diffusion-weighted MR size of ischemic areas in acute stroke patients with arterial recanalization. In all patients with a repermealized cerebral artery on the delayed angio-MR, the size of the final cerebral infarct defined on the delayed diffusion-weighted MR ranged between the admission perfusion-CT size of the cerebral infarct and the total ischemic area. This likely relates to an evolution of the infarct over the penumbra as defined on the admission perfusion-CT until arterial recanalization, followed by a recovery of the remaining penumbra.

FIG. 5. Correlation between the admission NIHSS and the combined infarct-penumbra size on the admission perfusion-CT. Admission NIHSS increased concomitantly with the initial size of the combined infarct and penumbra areas on the admission perfusion-CT ($_{perfusion-CT}$infarct+penumbra=5.953±0.222×$_{admission}$NIHSS; $r^2$=0.627). The more extensive the initial ischemic cerebral area, the worse the clinical condition, especially on admission when the mass effect consecutive to perilesional edema is preponderant.

FIG. 6. Correlation between the PRR and the NIHSS improvement in acute stroke patients with arterial recanalization. In patients with recanalization of the occluded cerebral artery, there was a strong correlation between the PAR and the improvement of the NIHSS evaluated on admission and after a 2.2±0.8-month time delay (NIHSS improvement=0.108+0.863×$_{prefusion-CT}$PRR; $r^2$=0.831). In these patients indeed, recanalization, whether spontaneous or consecutive to thrombolysis, allows to rescue the penumbra, with a subsequent and proportional improvement of the clinical condition.

The thresholds discussed in the subject application are not meant to be limiting to the present invention, but merely illustrate exemplary values that were generally found to yield the above stated results. Other values may be accorded to the variables discussed in the present invention upon realization of further consideration.

Having presented the present invention in view of the above described embodiments, various alterations, modifications, threshold values of CBV, CBF and MTT and improvements are intended to be within the scope and spirit of the invention. The foregoing description is by way of example only and is not intended as limiting. The invention's limit is defined only in the following claims and the equivalents thereto.

What is claimed is:

1. A method for creating a penumbra image of the brain of an acute stroke patient comprising:
    obtaining measurements of the brain of an acute stroke patient, said measurements including at least one of the cerebral blood flow, mean transit time, and cerebral blood volume;
    determining ischemic areas of the brain based on said measurements, wherein said ischemic areas are determined based on areas where cerebral blood flow is less than a predetermined first value less than a normal cerebral blood flow of an unaffected corresponding portion of the brain; and
    creating a map of penumbra areas, wherein said penumbra areas correspond to ischemic areas of the brain having cerebral blood volume greater than a predetermined second value.

2. The method according to claim 1, wherein infarct areas of the ischemic areas of the brain are established on said map, wherein said infarct areas correspond to areas of the brain where cerebral blood volume is less than said predetermined second value.

3. The method according to claim 2, further comprising determining a ratio between the size of said penumbra areas and the total size of said penumbra areas and said infarct areas of the brain, wherein when said ratio is greater than or equal to a predetermined third value, said acute stroke patient is a candidate for thrombolysis therapy.

4. The method according to claim 3, wherein said predetermined third value is greater than approximately 50%.

5. The method according to claim 3, wherein said predetermined third value is greater than approximately 65%.

6. The method according to claim 3, wherein said predetermined third value is greater than approximately 75%.

7. The method according to claim 1, wherein said predetermined first value for cerebral blood flow is less than approximately 90% of said normal blood cerebral blood flow of an unaffected corresponding portion of the brain.

8. The method according to claim 1, wherein said predetermined first value for cerebral blood flow is less than approximately 75% of said normal blood cerebral blood flow of an unaffected corresponding portion of the brain.

9. The method according to claim 1, wherein said predetermined first value for cerebral blood flow is less than approximately 60% of said normal blood cerebral blood flow of an unaffected corresponding portion of the brain.

10. The method according to claim 1, wherein said measurements are obtained using a computer tomography apparatus.

11. The method according to claim 1, wherein said predetermined second value for cerebral blood volume is between approximately 2 cc/100 grams of brain tissue and approximately 4 cc/100 grams of brain tissue.

12. A map of the brain of a stroke patient comprising: penumbra areas corresponding to areas of the brain having a cerebral blood volume of greater than a predetermined value.

13. The map according to claim 12, wherein said predetermined value is between approximately 2 cc/100 grams of brain tissue and approximately 4 cc/100 grams of brain tissue.

14. The map according to claim 12, further comprising infarct areas corresponding to areas of the brain having a cerebral blood volume of less than said predetermined value.

15. The map according to claim 14, wherein said predetermined value is between approximately 2 cc/100 g of brain tissue and approximately 4 cc/100 g of brain tissue.

16. The map according to claim 12, wherein a computer tomography apparatus is used to determine cerebral Hood volume of the brain of said patient.

17. The map according to claim 14, wherein said map quantifies the size of said infarct areas and said penumbra areas and quantifies a ratio of said penumbra size to the total of said penumbra size and said infarct size.

18. The map according to claim 12, wherein said map comprises a computer tomography image.

19. An apparatus for creating a penumbra image of the brain of an acute stroke patient comprising:
  measuring means for obtaining measurements of the brain of an acute stroke patient, said measurements including at least one of the cerebral blood flow, mean transit time and cerebral blood volume;
  determining means for determining ischemic areas of the brain based on said measurements, wherein said ischemic areas are determined based on areas where cerebral blood flow is less than a predetermined first value less than a normal cerebral blood flow of an unaffected corresponding portion of the brain; and
  mapping means for creating a map of penumbra areas, wherein said penumbra areas correspond to areas of the brain having cerebral blood volume greater than a predetermined second value.

20. The apparatus according to claim 19, wherein said map also comprises infarct areas corresponding to ischemic areas of the brain where cerebral blood volume is less than a predetermined second value.

21. The apparatus according to claim 20, wherein said determining means determines a ratio of the size of the penumbra areas to the total size of the penumbra areas and the infarct areas of the brain, and wherein when said ratio is above a predetermined third value, said acute stroke patient is a candidate for thrombolysis therapy.

22. The apparatus according to claim 19, further comprising display means for displaying said map.

23. Computer readable media having computer-executable instructions for performing a method comprising:
  obtaining measurements of the brain of an acute stroke patient, said measurements including at least one of the cerebral blood flow, mean transit time and cerebral blood volume;
  determining ischemic areas of the brain based on said measurements, wherein said ischemic areas are determined based on areas where cerebral blood flow is less than a predetermined first value less than a normal cerebral blood flow of an unaffected corresponding portion of the brain; and
  creating a map of penumbra areas, wherein said penumbra areas correspond to ischemic areas of the brain having cerebral blood volume greater than a predetermined second value.

24. A computerized method for creating a penumbra image of the brain of an acute stroke patient comprising:
  obtaining measurements of the brain of an acute stroke patient, said measurements including at least one of the cerebral blood flow, mean transit time and cerebral blood volume;
  determining ischemic areas of the brain based on said measurements, wherein said ischemic areas are determined based on areas where cerebral blood flow is less than a predetermined first value less than a normal cerebral blood flow of an unaffected corresponding portion of the brain; and
  creating a map of penumbra areas, wherein said penumbra areas correspond to ischemic areas of the brain having cerebral blood volume greater than a predetermined second value.

* * * * *